(12) United States Patent
Yonezawa et al.

(10) Patent No.: US 9,809,365 B2
(45) Date of Patent: Nov. 7, 2017

(54) WATER-SOLUBLE FILM, PACKAGING BAG, CONTENT RELEASE BODY, AND METHOD FOR PRODUCING WATER-SOLUBLE FILM

(71) Applicant: AICELLO CORPORATION, Toyohashi-shi, Aichi (JP)

(72) Inventors: Yuuki Yonezawa, Aichi (JP); Yuki Yasui, Aichi (JP)

(73) Assignee: AICELLO CORPORATION, Aichi (JP)

( * ) Notice: Subject to any disclaimer, the term of this patent is extended or adjusted under 35 U.S.C. 154(b) by 0 days.

(21) Appl. No.: 15/510,421

(22) PCT Filed: Sep. 8, 2015

(86) PCT No.: PCT/JP2015/075384
§ 371 (c)(1),
(2) Date: Mar. 10, 2017

(87) PCT Pub. No.: WO2016/039303
PCT Pub. Date: Mar. 17, 2016

(65) Prior Publication Data
US 2017/0259975 A1    Sep. 14, 2017

(30) Foreign Application Priority Data

Sep. 12, 2014   (JP) ................................ 2014-186708

(51) Int. Cl.
*B65D 65/46* (2006.01)
*B65D 65/02* (2006.01)
(Continued)

(52) U.S. Cl.
CPC ............. *B65D 65/46* (2013.01); *B65D 65/02* (2013.01); *C08J 5/18* (2013.01); *C08K 3/30* (2013.01);
(Continued)

(58) Field of Classification Search
CPC .. B65D 65/46; B65D 65/02; C08J 5/18; C08J 2329/04; C08K 3/30; C08K 2003/309
See application file for complete search history.

(56) References Cited

U.S. PATENT DOCUMENTS

2004/0161557 A1   8/2004  Verrall et al.
2008/0110370 A1   5/2008  Verrall et al.
(Continued)

FOREIGN PATENT DOCUMENTS

JP      5-306227 A    11/1993
JP      9-316258 A    12/1997
(Continued)

OTHER PUBLICATIONS

International Search Report dated Nov. 24, 2015 issued by the International Searching Authority in counterpart International Application No. PCT/JP2015/075384 (PCT/ISA/210).
(Continued)

*Primary Examiner* — Michael C Miggins
(74) *Attorney, Agent, or Firm* — Sughrue Mion, PLLC

(57) ABSTRACT

To provide a water-soluble film having excellent solubility, a packaging bag using the water-soluble film, a content release body using the water-soluble film, and a method for producing a water-soluble film. It is a water-soluble film prepared by film-forming a raw material containing a polyvinyl alcohol-based resin and a bisulfite. A bisulfite is added to the raw material containing the polyvinyl alcohol-based resin. Owing to this, the decrease in solubility of the water-soluble film is suppressed even though the raw material is maintained in a heating state for a predetermined time. This effect is the effect characteristic in a bisulfite, and is the effect that is not obtained in the case where a sulfite is used.

19 Claims, 1 Drawing Sheet

(51) Int. Cl.
*C08J 5/18* (2006.01)
*C08K 3/30* (2006.01)
(52) U.S. Cl.
CPC ..... *C08J 2329/04* (2013.01); *C08K 2003/309* (2013.01)

(56) References Cited

U.S. PATENT DOCUMENTS

| | | |
|---|---|---|
| 2008/0176985 A1 | 7/2008 | Verrall et al. |
| 2010/0105821 A1 | 4/2010 | Verrall et al. |
| 2013/0123165 A1 | 5/2013 | Gizaw et al. |
| 2013/0123166 A1 | 5/2013 | Gizaw et al. |

FOREIGN PATENT DOCUMENTS

| | | | |
|---|---|---|---|
| JP | 11-286892 A | 10/1999 |
| JP | 2002-20569 A | 1/2002 |
| JP | 2005-179390 A | 7/2005 |
| WO | 94/10233 A1 | 5/1994 |
| WO | 2008/064014 A2 | 5/2008 |
| WO | 2009/096164 A1 | 8/2009 |
| WO | 2013/070824 A1 | 5/2013 |

OTHER PUBLICATIONS

Written Opinion dated Nov. 24, 2015 issued by the International Searching Authority in counterpart International Application No. PCT/JP2015/075384 (PCT/ISA/237).

[FIG. 1]
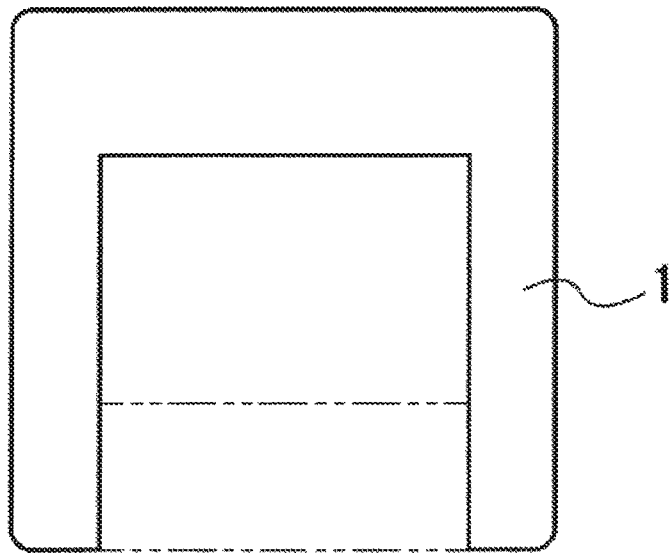
[FIG. 2]
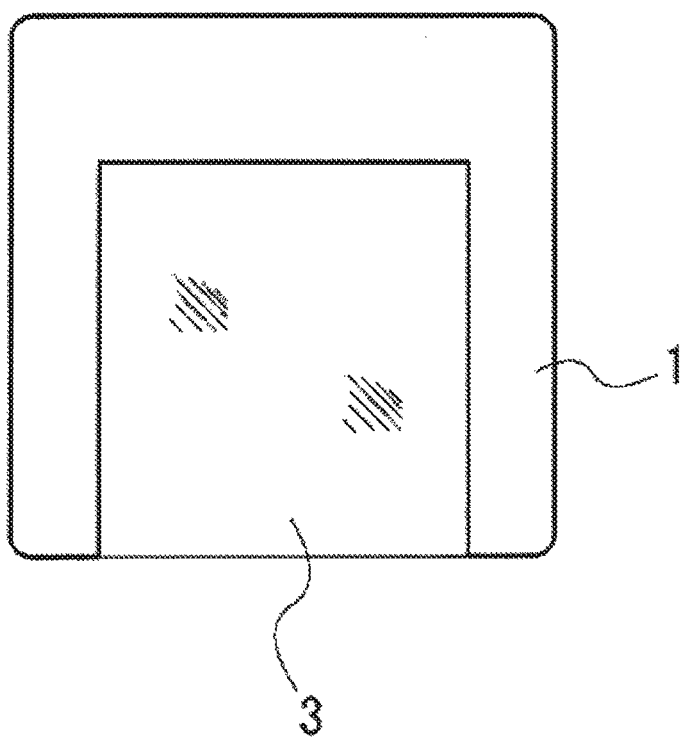

WATER-SOLUBLE FILM, PACKAGING BAG, CONTENT RELEASE BODY, AND METHOD FOR PRODUCING WATER-SOLUBLE FILM

TECHNICAL FIELD

The present invention relates to a water-soluble film, a packaging bag, a content release body, and a method for producing a water-soluble film.

BACKGROUND ART

A water-soluble film using a polyvinyl alcohol-based resin is widely utilized in uses (unit packing uses) of individually packaging chemicals such as a detergent, a cleaning agent, a disinfectant, an insecticide, a herbicide, a fertilizer, a dye, and an agricultural chemical, uses of a hydraulic transfer film, and other uses.

In the uses of individually packaging chemicals, it is not necessary to measure in each time when using chemicals, and this is very convenient to users. Therefore, it is expected that market scale of a water-soluble film in the uses is expanding.

However, in the water-soluble film conventionally used, the film gradually colors in pale yellow by thermal history received during film formation of a film, and there has been a concern that commercial value of a product is impaired.

In view of the above, a technology of incorporating two kinds of a plasticizer and a sulfite in a water-soluble film has been attempted (e.g., see Patent Document 1).

This technology discloses that a water-soluble film that is hardly colored at the time of film formation and hardly increases in coloration with time even when being brought into contact with chemicals can be obtained by incorporating two kinds of a plasticizer and a sulfite.

However, in the technology of this document, coloration is improved, but there is a case that solubility is insufficient, and further improvement is desired.

PRIOR ART DOCUMENT

Patent Document

Patent Document 1: JP-A-2005-179390

SUMMARY OF THE INVENTION

Problems that the Invention is to Solve

The present invention was made in view of the above circumstances, and has an object to provide a water-soluble film having excellent solubility, a packaging bag using the water-soluble film, a content release body using the water-soluble film, and a method for producing a water-soluble film.

Means for Solving the Problems

The present inventors made intensive studies in consideration of the above-described prior art, and as a result, they developed a novel water-soluble film.

In addition, they found an unexpected fact that this novel water-soluble film exhibits more excellent water-solubility than conventional water soluble-films. The present invention was made based on this finding.

That is, a first aspect of the invention:
a water-soluble film prepared by film-forming a raw material containing a polyvinyl alcohol-based resin and a bisulfite.

A second aspect of the present invention:
the water-soluble film according to the first aspect,
in which the bisulfite is a water solubility deterioration inhibitor.

A third aspect of the present invention:
the water-soluble film according to the first or second aspect, obtained by
maintaining the raw material containing the polyvinyl alcohol-based resin and the bisulfite in a heating state for a predetermined time, and
film-forming the raw material.

A fourth aspect of the present invention:
a packaging bag formed from the water-soluble film described in any one of the first to third aspects.

A fifth aspect of the present invention:
a content release body containing a content wrapped with the water-soluble film described in any one of the first to third aspects, and capable of releasing the content on contact with water.

A sixth aspect of the present invention:
a method for producing a water-soluble film, containing
maintaining a raw material containing a polyvinyl alcohol-based resin and a bisulfite in a heating state for a predetermined time, and
film-forming the raw material.

Advantageous Effect of the Invention

The water-soluble film of the present invention exhibits excellent water solubility.

As the water-soluble film having excellent water solubility is used, the packaging bag of the present invention can appropriately release the content.

As the water-soluble film having excellent water solubility is used, the content release body of the present invention can appropriately release the content.

According to the method for producing a water-soluble film of the present invention, a water-soluble film having excellent water solubility can be produced,

BRIEF DESCRIPTION OF DRAWINGS

The present invention is further described by the following detailed description by exemplifying non-limitative examples of typical embodiments of the present invention and while referring to a plurality of drawings referred thereto.

FIG. 1 It is an explanatory view illustrating a slide mount used in a dissolution test.

FIG. 2 It is an explanatory view illustrating the state where a water-soluble film has been set to a slide mount.

MODE FOR CARRYING OUT THE INVENTION

The matters described herein are exemplary matters and matters intended to illustratively explain embodiments of the present invention, and are described for the purpose of providing embodiments to be thought as the explanation that can understand the principle and conceptual features of the present invention most effectively and without difficulty. In this regard, these matters do not intend to show structural details of the present invention beyond the extent that is necessary for the fundamental understanding of the present invention, and are intended to clarify to one skilled in the art by the explanation coupled with the drawings as to how several embodiments of the present invention are actually embodied.

The embodiments of the present invention are described in detail below (1) Water-Soluble Film The water-soluble film of the present embodiment is prepared by film-forming a raw material containing a polyvinyl alcohol-based resin (hereinafter referred to as a "PVA-based resin") and a bisulfite.

<PVA-Based Resin>

The PVA-based resin used in the present embodiment is not particularly limited, and conventional PVA-based resins can be used. That is, resins obtained by saponifying a vinyl ester-type polymer obtained by polymerizing a vinyl ester-type compound can be widely used. In the present embodiment, not only one kind of the PVA-based resins, but two or more kinds thereof can be used hi combination.

As the vinyl ester-type compound, use can be made of one kind or two or more kinds of vinyl acetate, vinyl formate, vinyl trifluoroacetate, vinyl propionate, vinyl butyrate, vinyl caprate, vinyl laurate, vinyl versatate, vinyl palmitate, vinyl stearate, and the like.

In the PVA-based resin, an anionic group-modified PVA-based resin or a cationic group-modified PVA-based resin may be used. Of course, an unmodified PVA-based resin may be used.

An anionic group-modified PVA-based resin is preferred from the standpoint of solubility. The anionic group is not particularly limited, and examples thereof include a carboxyl group, a sulfonate group and a phosphate group.

The anionic group-modified PVA-based resin is not particularly limited, and examples thereof include a maleic acid-modified PVA-based resin, an itaconic acid-modified PVA-based resin, an acrylic acid-modified PVA-based resin, a methacrylic acid-modified PVA-based resin, and a 2-acrylamido-2-methylpropanesulfonic acid-modified PVA-based resin.

The amount of modification of the modified PVA-based resin is that the content of a modified unit is preferably from 0.1 to 10 mol %, more preferably from 0.5 to 8 mol %, and particularly preferably from 1 to 6 mol %. It is preferably 0.1 mol % or more from the standpoint of solubility in water, and is preferably 10 mol % or less from the standpoints of productivity and costs of a resin.

The PVA-based resin used in the present embodiment may have a repeating unit derived from the following monomers.

Examples thereof include olefins such as ethylene, propylene, isobutylene, α-octene, α-dodecene, and α-octadecene; complete alkyl esters of unsaturated acids such as acrylic acid, methacrylic acid, crotonic acid, maleic acid, maleic anhydride, and itaconic acid; nitriles such as acrylonitrile and methacrylonitrile; amides such as acrylamide and methacrylamide; alkyl vinyl ethers; N-acrylamidomethyltrimethylammonium chloride; allyltrimethylammonium chloride; dimethyldiallylammonium chloride; dimethylalylvinyl ketone, N-vinylpyrrolidone; vinyl chloride; vinylidene chloride; polyoxyalkylene (meth)allyl ether such as polyoxyethylene (meth)allyl ether and polyoxypropylene (meth)allyl ether; polyoxyalkylene (meth)acrylate such as polyoxyethylene (meth)acrylate and polyoxypropylene (meth)acrylate; polyoxyalkylene (meth)acryl amide such as polyoxyethylene (meth)acryl amide and polyoxypropylene (meth)acryl amide; polyoxyethylene (1-(meth)acryl amide-1,1-dimethylpropyl)ester; polyoxyethylene vinyl ether; polyoxypropylene vinyl ether, polyoxyethylene allylamine; polyoxypropylene allylamine; polyoxyethylene vinylamine; polyoxypropylene vinylamine, and diacrylacetone amide.

In the addition, the following cationic group-containing monomers can be also mentioned, for example, N-acrylamidomethyl trimethylammonium chloride, N-acrylamidoethyl trimethylammonium chloride, N-acrylamidopropyl trimethylammonium chloride, 2-acryloxyethyl trimethylammonium chloride, 2-methacryloxyethyl trimethylammonium chloride, 2-hydroxy-3-methacryloyloxypropyl trimethylammonium chloride, allyltrimethylammonium chloride, methallyltrimethylammonium chloride, 3-butenetrimethylammonium chloride, dimethyidiallylammonium chloride, and diethyldiallylammonium chloride.

In the present embodiment, these monomers can be contained within a range that does not impair the object of the present invention, for example, from 0.01 to 10 mol %.

An average degree of saponification of the PVA-based resin is not particularly limited. For example, it is preferably from 70 to 100 mol %, more preferably from 80 to 99 mol %, and particularly preferably from 87 to 98 mol %. When the average degree of saponification is within the above range, the effect of preventing the deterioration of water solubility by a bisulfite well appears.

The average degree of saponification is measured according to JIS K6726 3.5.

Viscosity of a 4 mass % aqueous solution of the PVA-based resin at 20° C. is not particularly limited. For example, it is preferably from 2.8 to 240 mPa·s, more preferably from 5 to 150 mPa·s, and particularly preferably from 8 to 50 mPa·s. This is because when the viscosity is within the above range, mechanical strength of a film and solubility of a film are particularly excellent. The viscosity of a 4 mass % aqueous solution is measured according to JIS K6726 3.11.2.

<Bisulfite>

The bisulfite used in the present embodiment is not particularly limited so long as it is a salt having a bisulfite ion. Examples thereof include sodium bisulfite, potassium bisulfite and ammonium bisulfite. Of those, sodium bisulfite is particularly preferred from the standpoint of solubility of the water-soluble film. The bisulfite may be used in one kind alone or used as a mixture of two or more kinds.

In the present embodiment, the bisulfite is used as a water solubility deterioration inhibitor of the water-soluble film. The content (total amount) of the bisulfite in the water-soluble film is not particularly limited. For example, it is preferably from 0.01 to 30 parts by mass, more preferably from 0.5 to 20 parts by mass, and particularly preferably from 0.5 to 5 parts by mass, per 100 parts by mass of the PVA-based resin. This is because when the content is within this range, the improvement effect of water solubility can be sufficiently obtained, and additionally, sufficient film strength can be obtained.

<Other Components>

[Plasticizer]

In the present embodiment, a plasticizer can be contained in the raw material. The plasticizer is not particularly limited, and the conventional plasticizers can be applied. Examples thereof include polyhydric alcohol-based plasticizers such as glycerin; polyglycerin such as diglycerin; sugar such as glucose, fructose, lactose, sorbitol, tar mannitol; sugar alcohol; low molecular weight polyethylene glycol (molecular weight: 600 or less); ethylene glycol; propylene glycol; trimethylolpropane; and 2-methyl-1,3-propanediol. The plasticizer may be use in one kind alone or used as a mixture of two or more kinds.

The content (total amount) of the plasticizer in the water-soluble film is not particularly limited. For example, it is preferably from 0 to 50 parts by mass, more preferably from 5 to 40 parts by mass, and particularly preferably from 8 to 30 parts by mass, per 100 parts by mass of the PVA-based resin. This is because when the content is within this range, the plasticization effect can be obtained, the plasticizer is suppressed from bleeding on a film surface, and additionally, sufficient film strength can be obtained.

[Surfactant]

In the present embodiment, a surfactant can be contained in the raw material. The surfactant is not particularly limited, and the conventional surfactants can be applied. As the surfactant, an ionic surfactant (anionic surfactant, cationic surfactant and amphoteric surfactant), a nonionic surfactant, or a polymeric surfactant can be applied. The surfactant may be used in one kind alone or used as a mixture of two or more kinds.

The content of the surfactant is not particularly limited. It is preferably from 0.01 to 3.0 parts by mass, more preferably from 0.03 to 2.5 parts by mass, and particularly preferably from 0.05 to 1.5 parts by mass, per 100 parts by mass of the PYA-based resin. This is because when the content is within this range, handling of a film at the time of film formation of a water-soluble film becomes easy, and productivity is improved.

[Additives]

In the present embodiment, various additives can be contained in the raw material. As necessary, a colorant, a perfume, an extending agent, a defoaming agent, a release agent, an UV absorber, an inorganic powder, and the like are used as the additives.

Furthermore, an inorganic filler and an organic filler can be contained in the raw material. The inorganic filler is not particularly limited. Examples thereof include silica, talc, clay, hydrotalcite, diatomaceous earth, kaolin, mica, gypsum, graphite, glass balloon, glass beads, calcium sulfate, barium sulfate, ammonium sulfate, calcium sulfite, calcium carbonate, whisker-like calcium carbonate, magnesium oxide, magnesium hydroxide, zinc oxide, magnesium carbonate, dawsonite, dolomite, potassium titanate, carbon black, glass fiber, alumina fiber, boron fiber, processed mineral liber, carbon fiber, carbon hollow sphere, bentonite, montmorillonite, copper powder, sodium sulfate, potassium sulfate, zinc sulfate, copper sulfate, iron sulfate, magnesium sulfate, aluminum sulfate, aluminum potassium sulfate, ammonium nitrate, sodium nitrate, potassium nitrate, aluminum nitrate, ammonium chloride, sodium chloride, potassium chloride, magnesium chloride, calcium chloride, sodium phosphate, potassium chromate, and calcium citrate.

The organic filler is not particularly limited, and examples thereof include starch, and various resins such as a melamine-based resin.

The content of the filler is not particularly limited. It is preferably from 0 to 100 parts by mass, more preferably from 0.1 to 50 parts by mass, and particularly preferably from 1 to 10 parts by mass, per 100 parts by mass of the PVA-based resin. By adding the filler, antiblocking property of the water-soluble resin may be improved or the filler may act as a dissolution assistant of the watersoluble film in some cases.

The PVA-based resin may be mixed with another water-soluble polymer. Examples of the water-soluble polymer include gelatin, casein, gum Arabic, polyvinyl pyrrolidone, pullulan, methyl cellulose, hypromellose, and ethyl cellulose. The amount of the water-soluble polymer added is preferably 20 parts by mass or less per 100 parts by mass of the PVA-based resin.

Water may be added to the raw material. The amount of water added is not particularly limited. It is generally from 25 to 10000 parts by mass, and more preferably from 40 to 1000 parts by mass, per 100 parts by mass of the PVA-based resin. This is because within this range, the film formation efficiency of the water-soluble film is improved.

[Thickness and the Like of Water-Soluble Film]

The thickness of the water-soluble film is not particularly limited. It is preferably from 10 to 100 μm, more preferably from 20 to 100 μm, and particularly preferably from 30 to 90 μm. This is because when the thickness is within this range, excellent water solubility can be exhibited while appropriately maintaining strength of the water-soluble film.

The surface shape of the water-soluble film is not particularly limited. For example, it may be flat (plane), and emboss pattern, satin pattern or the like may be given to one surface or both surfaces of the film.

[Solubility]

The evaluation of solubility of the water-soluble film is conducted by the following test method. Dissolution time is measured with this method, and the change rate of dissolution time per 24 hour-heating of the raw material is calculated by the following formula.

In the case of heating the raw material at 85° C. and in the case of using the water-soluble film having a thickness of 75 μm, for example, the change rate is preferably $0.001 \leq R \leq 1.4$, more preferably $0.001 \leq R \leq 1.3$, and particularly preferably $0.001 \leq R \leq 1.2$.

$$R=(S_2-S_1)\div(T_2-T_1)\times 24 \quad \text{(Formula)}$$

Change rate of dissolution time per 24 hour-heating: R

Heating time: $T_1$ (h)

Heating time: $T_2$ (h) (here, $T_1 < T_2$)

Dissolution time of film using raw material of heating time $T_1$: $S_1$ (s)

Dissolution time of film using raw material of heating time $T_2$: $S_2$ (s)

(Test Method)

As illustrated in FIG. 1, a long side part of a slide mount (FUJI COLOR, plastic mount for 35 mm) is cut to form a nearly inverse U-shape. A film of 3.5 cm×3.9 cm, which is larger than an opening, is attached thereto as illustrated in FIG. 2. That is, three sides of the film are fixed to a frame of the slide mount.

The slide mount having the film attached thereto is dipped in the state of a nearly inverse U-shape in a 1000 ml beaker having 800 ml of 10° C. water therein until the entire surface of the film is submerged under the water, and stopped. They are allowed to stand in the state, and time until the film dissolves and falls down from the slide mount is defined as a dissolution time.

<Film Formation>

In film-forming the raw material, the production method is not particularly limited, and the conventional production method of a film can be applied. For example, use can be made of a solvent casting process (solution casting process) that obtains a film by flow casting a raw material dissolved in a solvent (water) on a band made of a metal or the like or on a drum made of a metal or the like, and removing the solvent by drying. In this method, the solid content concentration of a resin composition in flow casting is not particularly limited. For example, the solid content concentration is from 1 to 80 mass %, Drying temperature in this production method, that is, a surface temperature of the band made of a metal or the like or the drum made of a metal or the like is not particularly limited, but is generally from 50 to 100° C., and preferably from 60 to 99° C. Furthermore, drying time is not also limited in particular, but is generally from 1 minute to 1 hour.

Furthermore, also applicable is a melt extrusion process in which a raw material is heated to a melting point or higher of the PVA-based resin, melt-kneaded, extruded from a die, and cooled to obtain a film.

In the present embodiment, after a raw material containing a PVA-based resin and a bisulfite is maintained in a heating state for a predetermined time, the raw material may be film-formed.

The temperature in the heating state is appropriately selected depending on the kind of the PVA-based resin, and the like. For example, it is generally from 30 to 100° C., preferably from 60 to 99° C., and particularly from 70 to 99° C.

The time period of maintaining in the heating state is not particularly limited. For example, it is generally from 1 minute to 360 hours, preferably from 30 minutes to 288 hours, and particularly from 1 to 240 hours.

The method for maintaining in the heating state for the predetermined time is not particularly limited. The case of maintaining in a tank or maintaining in a piping is exemplified. For example, a hatch-type dissolution tank can be used as the tank.

When the raw material containing the PVA-based resin is maintained in a heating state for a predetermined time, and then film-formed to obtain a water-soluble film, there was a tendency that solubility is decreased.

In the present embodiment, a bisulfite is added to the raw material containing the PVA-based resin. By this, there is a tendency that the decrease in solubility of the water-soluble film is suppressed even though a film has been formed after maintaining the raw material in a heating state for a predetermined time. This tendency is remarkable in the case of using an anionic group-modified PVA resin rather than an unmodified PVA-based resin.

This effect is the effect characteristic in a bisulfite, and is the effect that is not obtained in the case where a sulfite is used.

<Effect of Water-Soluble Film of the Present Embodiment>

The water-soluble film of the present embodiment exhibits the following action and effect. That is, there was a tendency that solubility is decreased in a water-soluble film that is film-formed after maintaining the raw material containing the PVA-based resin in a heating state for a predetermined time.

In the present embodiment, since a bisulfite is added to the raw material containing the PVA-based resin, the decrease in solubility of the water-soluble film is suppressed even though the raw material is maintained in a heating state for a predetermined time.

The reason why the decrease in solubility of the water-soluble film is suppressed is not clear, but it is assumed as follows. That is, it is assumed that an intramolecular lactonization reaction of the PVA-based resin is suppressed and an intermolecular crosslinking reaction of the PVA-based resin is suppressed, by a bisulfite, and as a result, the decrease in solubility of the water-soluble film is suppressed.

[2] Packaging Bag

The packaging bag of the present embodiment is characterized in that it is formed from the water-soluble film described above. The packaging bag of the present embodiment is to wrap a content. The content is not particularly limited. For example, chemicals such as a detergent, a cleaning agent, a disinfectant, an insecticide, a herbicide, a fertilizer, a dye, and an agricultural chemical are used as the content, A shape, size and the like of the packaging bag can be appropriately selected depending on the kind, amount and the like of the content.

<Effect of Packaging Bag of the Present Embodiment>

The packaging bag of the present embodiment exhibits the following action and effect. That is, there were some cases that it cannot always be said that the solubility of the packaging bag using the conventional water-soluble film is sufficient. In the packaging bag of the present embodiment, since a bisulfite is added to the raw material containing the PVA-based resin, the decrease in solubility of the water-soluble film is suppressed, and the content is quickly released from the packaging bag.

[3] Content Release Body

The content release body of the present embodiment contains a content wrapped with the water-soluble film described above, and is a content release body capable of releasing the content on contact with water. As the content, that explained in the item of [2] Packaging bag described above can be used. That is, the content is not particularly limited, and for example, chemicals such as a detergent, a cleaning agent, a disinfectant, an insecticide, a herbicide, a fertilizer, a dye, and an agricultural chemical can be used.

A shape, size and the like of the content release body can be appropriately selected depending on the kind, amount and the like of the content.

<Effect of Content Release Body of the Present Embodiment>

The content release body of the present embodiment exhibits the following action and effect. That is, there were some cases that it cannot always be said that the solubility of the content release body using the conventional water-soluble film is sufficient. In the content release body of the present embodiment, since a bisulfate is added to the raw material containing the PVA-based resin, the decrease in solubility of the water-soluble film is suppressed, and the content is quickly released from the content release body.

[4] Method for Producing Water-Soluble Film

The method for producing a water-soluble film, according to the present embodiment is characterized by maintaining a raw material containing a polyvinyl alcohol-based resin and a bisulfite in a heating state for a predetermined time, and then film-forming the raw material.

In the method for producing a water-soluble film of the present embodiment, "polyvinyl alcohol-based resin", "bisulfite", "other components", "film formation" and the like can apply the explanations in [1] Water-soluble film described above as those are.

<Effect of Method for Producing Water-Soluble Film of the Present Embodiment>

In the method for producing a water-soluble film of the present embodiment, since a bisulfite is added to the raw material containing the PVA-based resin, the decrease in solubility of the water-soluble film can be suppressed even though film-formed after maintaining the raw material in a heating state for a predetermined time.

EXAMPLES

The present invention is described in further detail below by reference to examples.

[1] Preparation of Water-Soluble Film

Example 1

Maleic acid-modified PVA having 4% aqueous solution viscosity of 12.0 mPa·s (20° C.), average degree of saponification of 88 mol % and amount of modification of 2.0 mol % was used as a PVA-based resin. To 100 parts by mass of the PVA-based resin were added 16 parts by mass of glycerin as a plasticizer, 0.1 parts by mass of sodium bisulfite, 0.5 parts by mass of an anionic surfactant, and water, to obtain an aqueous solution of a resin composition.

The aqueous solution was maintained at 85° C. for 24 hours, and then formed by a solution casting method to obtain a water-soluble film (Sample 1) having a thickness of 75 μm.

The same aqueous solution was maintained at 85° C. for 168 hours, and then formed by a solution casting method to obtain a water-soluble film (Sample 2) having a thickness of 75 μm.

Example 2

An aqueous solution was obtained in the same manner as in Example 1, except that the content of sodium bisulfite was changed to 0.5 parts by mass.

The aqueous solution was maintained at 85° C. for 24 hours, and then formed by a solution casting method to obtain a water-soluble film (Sample 3) having a thickness of 75 μm.

The same aqueous solution was maintained at 85° C. for 168 hours, and then formed by a solution casting method to obtain a water-soluble film (Sample 4) having a thickness of 75 μm.

Example 3

An aqueous solution was obtained in the same manner as in Example 1, except that the content of sodium bisulfite was changed to 1.0 part by mass.

The aqueous solution was maintained at 85° C. for 24 hours, and then formed by a solution casting method to obtain a water-soluble film (Sample 5) having a thickness of 75 μm.

The same aqueous solution was maintained at 85° C. for 168 hours, and then formed by a solution casting method to obtain a water-soluble film (Sample 6) having a thickness of 75 μm.

Example 4

An aqueous solution was obtained in the same manner as in Example 1, except that the content of sodium bisulfite was changed to 1.5 parts by mass.

The aqueous solution was maintained at 85° C. for 24 hours, and then formed by a solution casting method to obtain a water-soluble film (Sample 7) having a thickness of 75 μm.

The same aqueous solution was maintained at 85° C. for 168 hours, and then formed by a solution casting method to obtain a water-soluble film (Sample 8) having a thickness of 75 μm.

Example 5

An aqueous solution was obtained in the same manner as in Example 1, except that the content of sodium bisulfite was changed to 2.0 parts by mass.

The aqueous solution was maintained at 85° C. for 24 hours, and then formed by a solution casting method to obtain a water-soluble film (Sample 9) having a thickness of 75 μm.

The same aqueous solution was maintained at 85° C. for 168 hours, and then formed by a solution casting method to obtain a water-soluble film (Sample 10) having a thickness of 75 μm.

Example 6

An aqueous solution was obtained in the same manner as in Example 1, except that the content of sodium bisulfite was changed to 5.0 parts by mass.

The aqueous solution was maintained at 85° C. for 24 hours, and then formed by a solution casting method to obtain a water-soluble film (Sample 11) having a thickness of The same aqueous solution was maintained at 85° C. for 168 hours, and then formed by a solution casting method to obtain a water-soluble film (Sample 12) having a thickness of 75 μm.

Example 7

An aqueous solution was obtained in the same manner as in Example 1, except that the content of sodium bisulfite was changed to 10 parts by mass.

The aqueous solution was maintained at 85° C. for 24 hours, and then formed by a solution casting method to obtain a water-soluble film (Sample 13) having a thickness of 75 μm.

The same aqueous solution was maintained at 85° C. for 168 hours, and then formed by a solution casting method to obtain a water-soluble film (Sample 14) having a thickness of 75 μm.

Example 8

An aqueous solution was obtained in the same manner as in Example 1, except that the content of sodium bisulfite was changed to 15 parts by mass.

The aqueous solution was maintained at 85° C. for 24 hours, and then formed by a solution casting method to obtain a water-soluble film (Sample 15) having a thickness of 75 μm.

The same aqueous solution was maintained at 85° C. for 168 hours, and then formed by a solution casting method to obtain a water-soluble film (Sample 16) having a thickness of 75 μm.

Example 9

An aqueous solution was obtained in the same manner as in Example 1, except that the content of sodium bisulfite was changed to 20 parts by mass.

The aqueous solution was maintained at 85° C. for 24 hours, and then formed by a solution casting method to obtain a water-soluble film (Sample 17) having a thickness of 75 μm.

The same aqueous solution was maintained at 85° C. for 168 hours, and then formed by a solution casting method to obtain a water-soluble film (Sample 18) having a thickness of 75 μm.

Example 10

Maleic acid-modified PVA having 4% aqueous solution viscosity of 28.0 mPa·s (20° C.), average degree of saponification of 88 mol % and amount of modification of 2.0 mol % was used as a PVA-based resin. To 100 parts by mass of the PVA-based resin were added 21 parts by mass of glycerin as a plasticizer, 1.5 parts by mass of sodium bisulfite, 0.5 parts by mass of an anionic surfactant, and water, to obtain an aqueous solution of a resin composition.

The aqueous solution was maintained at 85° C. for 24 hours, and then formed by a solution casting method to obtain a water-soluble film (Sample 19) having a thickness of 75 μm.

The same aqueous solution was maintained at 85° C. for 1.68 hours, and then formed by a solution casting method to obtain a water-soluble film (Sample 20) having a thickness of 75 μm.

Comparative Example 1

Maleic acid-modified PVA having 4% aqueous solution viscosity of 12.0 mPa·s (20° C.), average degree of saponification of 88 mol % and amount of modification of 2.0 mol % was used as a PVA-based resin. To 100 parts by mass of the PVA-based resin were added 16 parts by mass of glycerin as a plasticizer, 0.5 parts by mass of an anionic surfactant and water, to obtain an aqueous solution of a resin composition.

The aqueous solution was maintained at 85° C. for 24 how's, and then formed by a solution casting method to obtain a water-soluble film (Sample 21) having a thickness of 75 μm.

The same aqueous solution was maintained at 85° C. for 168 hours, and then formed by a solution casting method to obtain a water-soluble film (Sample 22) having a thickness of 75 μm.

Comparative Example 2

Maleic acid-modified PVA having 4% aqueous solution viscosity of 12.0 mPa·s (20° C.), average degree of saponification of 88 mol % and amount of modification of 2.0 mol % was used as a PVA-based resin. To 100 parts by mass of the PVA-based resin were added 16 parts by mass of glycerin as a plasticizer, 2.0 parts by mass of sodium sulfite, 0.5 parts by mass of an anionic surfactant, and water, to obtain an aqueous solution of a resin composition.

The aqueous solution was maintained at 85° C. for 24 hours, and then formed by a solution casting method to obtain a water-soluble film (Sample 23) having a thickness of 75 μm.

The same aqueous solution was maintained at 85° C. for 168 hours, and then formed by a solution casting method to obtain a water-soluble film (Sample 24) having a thickness of 75 μm.

Comparative Example 3

Maleic acid-modified PVA having 4% aqueous solution viscosity of 28.0 mPa·s (20° C.), average degree of saponification of 88 mol % and amount of modification of 2.0 mol % was used as a PVA-based resin. To 100 parts by mass of the PVA-based resin were added 21 parts by mass of glycerin as a plasticizer, 1.5 parts by mass of sodium sulfite, 0.5 parts by mass of an anionic surfactant, and water, to obtain an aqueous solution of a resin composition.

The aqueous solution was maintained at 85° C. for 24 hours, and then formed by a solution casting method to obtain a water-soluble film (Sample 25) having a thickness of 75 μm.

The same aqueous solution was maintained at 85° C. for 168 hours, and then formed by a solution casting method to obtain a water-soluble film (Sample 26) having a thickness of 75 μm.

[2] Test of Solubility

The water-soluble films (Samples 1 to 26) of Examples 1 to 10 and Comparative Examples 1 to 3 were subjected to a solubility test by using the above-described test method.

The results are shown in Table 1. In Examples 1 to 10 using sodium bisulfite, solubility of the water-soluble film was good even though the aqueous solution was maintained at 85° C. That is, the change rate of dissolution time per 24 hour-heating was suppressed low.

On the other hand, in Comparative Example 1 of additive-free and Comparative Examples 2 to 3 using sodium sulfite, the decrease in solubility of the water-soluble film was remarkable when the aqueous solution was maintained at 85° C. That is, the change rate of dissolution time per 24 hour-heating was higher than the cases of Examples.

In more detail, in the comparison between the cases of Examples 1 to 9 and the cases of Comparative Examples 1 to 2, using the same PVA-based resin, the change rate of dissolution time per 24 hour-heating was suppressed 1.0 or lower in the cases of Examples 1 to 9. On the other hand, the change rate of dissolution time per 24 hour-heating was high as 1.8 in Comparative Example 1 in which a water solubility deterioration inhibitor was not added. Furthermore, the change rate of dissolution time per 24 hour-heating was high as 1.5 in Comparative Example 2 in which 2.0 parts by mass of sodium sulfite was added. In the cases of Examples 1 to 9, it has been found that the amount of the sodium bisulfite added is particularly preferably from 0.5 to 5.0 parts by mass from the standpoint of solubility, and the standpoints of production cost and the like.

In the comparison between the case of Example 10 and the case of Comparative Example 3, using the same PVA-based resin, the change rate of dissolution time per 24 hour-heating was suppressed 0.5 in the case of Example 10. On the other hand, the change rate of dissolution time per 24 hour-heating was high as 1.8 in Comparative Example 3 in which 1.5 parts by mass of sodium sulfite was added.

TABLE 1

| Water-soluble film | | 4% Aqueous solution viscosity of polyvinyl alcohol (mPa·s) | Amount of glycerin added (parts by mass) | Additives Kind of additives | Addition amount (parts by mass) | Solubility at 10° C. of film having thickness of 75 μm | | Change rate of dissolution time per 24 hour-heating (sec/24 hrs) |
|---|---|---|---|---|---|---|---|---|
| | | | | | | Heating time of aqueous solution at 85° C. | | |
| | | | | | | 24 hrs Dissolution time (sec) | 168 hrs | |
| Ex. 1 | Samples 1, 2 | 12 | 16 | Sodium bisulfite | 0.1 | 67 | 73 | 1.0 |
| Ex. 2 | Samples 3, 4 | | | | 0.5 | 63 | 67 | 0.7 |
| Ex. 3 | Samples 5, 6 | | | | 1.0 | 61 | 64 | 0.5 |
| Ex. 4 | Samples 7, 8 | | | | 1.5 | 60 | 63 | 0.5 |
| Ex. 5 | Samples 9, 10 | | | | 2.0 | 59 | 62 | 0.5 |
| Ex. 6 | Samples 11, 12 | | | | 5.0 | 57 | 60 | 0.5 |
| Ex. 7 | Samples 13, 14 | | | | 10 | 56 | 58 | 0.3 |
| Ex. 8 | Samples 15, 16 | | | | 15 | 55 | 57 | 0.3 |
| Ex. 9 | Samples 17, 18 | | | | 20 | 55 | 57 | 0.3 |
| Ex. 10 | Samples 19, 20 | 28 | 21 | Sodium bisulfite | 1.5 | 66 | 69 | 0.5 |
| Comp. Ex. 1 | Samples 21, 22 | 12 | 16 | — | 0 | 69 | 80 | 1.8 |
| Comp. Ex. 2 | Samples 23, 24 | | | Sodium sulfite | 2.0 | 64 | 73 | 1.5 |
| Comp. Ex. 3 | Samples 25, 26 | 28 | 21 | Sodium sulfite | 1.5 | 68 | 79 | 1.8 |

<Effects of Examples>

It has been found from the above results that even though the aqueous solution containing theINA-based resin is maintained in a heating state, the decrease in solubility in cooled water of the water-soluble film is remarkably suppressed by the addition of sodium bisulfite.

The above-described examples are only intended merely for the purpose of explanation and are not intended to be construed as limiting the present invention. While the present invention has been described by referring to examples of typical embodiments, the language used in the description and illustration of the present invention is understood to be illustrative and exemplary rather than restrictive wording. As described in detail herein, the modification can be made within the scope of the appended claims without departing from the scope and spirit of the present invention in its embodiment. Here, the specific structure, material and examples have been referred to in the detailed description of the present invention, but those are not intended to limit the present invention to the disclosure herein, and rather the present invention covers all of functionally equivalent structures, methods and uses within the scope of the appended claims.

The present invention is not limited to the embodiments described in detail above, and can be various modified or changed in the scope shown in the claims of the present invention.

The preferred embodiments of the present invention are described below.

[1] A water-soluble film prepared by film-forming a raw material containing a polyvinyl alcohol-based resin and a bisulfite, in which
the bisulfite is a water solubility deterioration inhibitor, and
the polyvinyl alcohol-based resin contains at least one kind selected from the group consisting of a maleic acid-modified PVA-based resin, an itaconic acid-modified PVA-based resin, an acrylic acid-modified PVA-based resin, and a methacrylic acid-modified PVA-based resin, as an anionic group-modified PVA-based resin.

[2] The water-soluble film according to [1], in which the amount of a water-soluble polymer added other than the polyvinyl alcohol-based resin in the raw material is 20 parts by mass or less per 100 parts by mass of the polyvinyl alcohol-based resin.

[3] The water-soluble film according to [1] or [2], obtained by
maintaining the raw material containing the polyvinyl alcohol-based resin and the bisulfite in a heating state for a predetermined time, and
film-forming the raw material.

[4] A packaging bag formed from the water-soluble film described in any one of [1] to [3].

[5] A content release body containing a content wrapped with the water-soluble film described in any one of [1] to [3], and capable of releasing the content on contact with water.

[6] A method for producing a water-soluble film, containing maintaining a raw material containing a polyvinyl alcohol-based resin and a bisulfite as a water solubility deterioration inhibitor in a heating state for a predetermined time, and
film-forming the raw material,
in which the polyvinyl alcohol-based resin contains at least one kind selected from the group consisting of a maleic acid-modified PVA-based resin, an itaconic acid-modified PVA-based resin, an acrylic acid-modified PVA-based resin, and a methacrylic acid-modified PVA-based resin, as an anionic group-modified PVA-based resin.

INDUSTRIAL APPLICABILITY

The present invention is widely applied to uses (unit packing uses) of individually packaging chemicals such as a detergent, a cleaning agent, a disinfectant, an insecticide, a herbicide, a fertilizer, a dye, and an agricultural chemical, uses of a hydraulic transfer film, and other uses.

DESCRIPTION OF REFERENCE NUMERALS AND SIGNS

1: Slide mount
3: Water-soluble film

The invention claimed is:

1. A water-soluble film prepared by film-forming a raw material comprising a polyvinyl alcohol-based resin and a bisulfite,
wherein the polyvinyl alcohol-based resin comprises at least one anionic group-modified PVA-based resin selected from the group consisting of a maleic acid-modified PVA-based resin, an itaconic acid-modified PVA-based resin, an acrylic acid-modified PVA-based resin, and a methacrylic acid-modified PVA-based resin.

2. The water-soluble film according to claim 1,
wherein the bisulfite is a water solubility deterioration inhibitor.

3. The water-soluble film according to claim 1, obtained by
maintaining the raw material comprising the polyvinyl alcohol-based resin and the bisulfite in a heating state for a predetermined time, and
film-forming the raw material.

4. The water-soluble film according to claim 1,
wherein the raw material further comprises a water-soluble polymer in an amount of 20 parts by mass or less per 100 parts by mass of the PVA-based resin.

5. The water-soluble film according to claim 1,
wherein the bisulfite comprises at least one kind selected from the group consisting of sodium bisulfite, potassium bisulfite and ammonium bisulfite.

6. The water-soluble film according to claim 1,
wherein when the raw material is maintained at 85° C. and the water-soluble film is formed to have a thickness of 75 μm, R represented by the following formula satisfies 0.001≤R≤1.4:

$R=(S_2-S_1)\div(T_2-T_1)\times 24$

Change rate of dissolution time per 24 hour-heating: R
Heating time: $T_1$ (h)
Heating time: $T_2$ (h) (here, $T_1<T_2$)
Dissolution time of film using raw material of heating time $T_1$: $S_1$ (s)
Dissolution time of film using raw material of heating time $T_2$: $S_2$ (s).

7. A packaging bag formed from the water-soluble film described in claim 1.

8. A content release body comprising a content wrapped with the water-soluble film described in claim 1, and capable of releasing the content on contact with water.

9. A method for producing a water-soluble film, comprising
maintaining a raw material comprising a polyvinyl alcohol-based resin and a bisulfite in a heating state for a predetermined time, and
film-forming the raw material,
wherein the polyvinyl alcohol-based resin comprises at least one anionic group-modified PVA-based resin selected from the group consisting of a maleic acid-modified PVA-based resin, an itaconic acid-modified PVA-based resin, an acrylic acid-modified PVA-based resin, and a methacrylic acid-modified PVA-based resin.

10. The method for producing a water-soluble film according to claim 9, wherein the temperature of the heating state is in a range of from 60° C. to 100° C.

11. The method for producing a water-soluble film according to claim 9, wherein the time period of the predetermined time is in a range of from 1 hour to 360 hours.

12. A water-soluble film comprising a polyvinyl alcohol-based resin and a bisulfite,
wherein the polyvinyl alcohol-based resin comprises at least one anionic group-modified PVA-based resin selected from the group consisting of a maleic acid-modified PVA-based resin, an itaconic acid-modified PVA-based resin, an acrylic acid-modified PVA-based resin, and a methacrylic acid-modified PVA-based resin.

13. The water-soluble film according to claim 12,
wherein the bisulfite is a water solubility deterioration inhibitor.

14. The water-soluble film according to claim 12, obtained by
maintaining the raw material comprising the polyvinyl alcohol-based resin and the bisulfite in a heating state for a predetermined time, and
film-forming the raw material.

15. The water-soluble film according to claim 12,
wherein the raw material further comprises a water-soluble polymer in an amount of 20 parts by mass or less per 100 parts by mass of the PVA-based resin.

16. The water-soluble film according to claim 12,
wherein the bisulfite comprises at least one kind selected from the group consisting of sodium bisulfite, potassium bisulfite and ammonium bisulfite.

17. The water-soluble film according to claim 12,
wherein when the raw material is maintained at 85° C. and the water-soluble film is formed to have a thickness of 75 μm, R represented by the following formula satisfies 0.001≤R≤1.4:

$R=(S_2-S_1)\div(T_2-T_1)\times 24$

Change rate of dissolution time per 24 hour-heating: R
Heating time: $T_1$ (h)
Heating time: $T_2$ (h) (here, $T_1<T_2$)
Dissolution time of film using raw material of heating time $T_1$: $S_1$ (s)
Dissolution time of film using raw material of heating time $T_2$: $S_2$ (s).

18. A packaging bag formed from the water-soluble film described in claim 12.

19. A content release body comprising a content wrapped with the water-soluble film described in claim 12, and capable of releasing the content on contact with water.

* * * * *